(12) United States Patent
Axelrod et al.

(10) Patent No.: US 7,959,905 B2
(45) Date of Patent: Jun. 14, 2011

(54) TAMANU OIL PRODUCTS

(75) Inventors: Glen S. Axelrod, Colts Neck, NJ (US); Ajay Gajria, Monmouth Junction, NJ (US)

(73) Assignee: T.F.H. Publications, Inc., Neptune City, NJ (US)

( * ) Notice: Subject to any disclaimer, the term of this patent is extended or adjusted under 35 U.S.C. 154(b) by 1405 days.

(21) Appl. No.: 11/423,398

(22) Filed: Jun. 9, 2006

(65) Prior Publication Data

US 2007/0286838 A1     Dec. 13, 2007

(51) Int. Cl.
*A61K 36/28* (2006.01)
*A61K 8/97* (2006.01)
*A61K 31/355* (2006.01)
*A61K 31/07* (2006.01)
*A61K 31/202* (2006.01)
*A61K 8/00* (2006.01)

(52) U.S. Cl. ......... 424/70.1; 424/74; 424/764; 424/776; 514/458; 514/560; 514/725

(58) Field of Classification Search .................. 424/70.1
See application file for complete search history.

(56) References Cited

U.S. PATENT DOCUMENTS

| 5,660,865 | A | 8/1997 | Pedersen et al. |
| 5,906,825 | A | 5/1999 | Seabrook, Jr. et al. |
| 6,964,954 | B2 | 11/2005 | Dalko et al. |
| 2003/0113284 | A1 | 6/2003 | Dalko et al. |
| 2003/0224028 | A1 | 12/2003 | Galey |
| 2004/0001897 | A1 | 1/2004 | Amano et al. |
| 2004/0101503 | A1* | 5/2004 | Mahe et al. ................. 424/70.14 |
| 2005/0136079 | A1 | 6/2005 | Burangulov et al. |

OTHER PUBLICATIONS

Frank S. D'Amelio. Botanicals: A Phytocosmetic Desk Reference. pp. 57-58. 1999.*
Dweck et al. Tamanu (*Calophyllum inophyllum*)—the African, Asian, Polynesian and Pacific Panacea. International Journal of Cosmetic Science. 2002.*
International Search Report and Written Opinion of the International Searching Authority issued in the counterpart International Appln. No. PCT/US07/70779 filed Jun. 8, 2007; date of mailing of ISR & W/O: Dec. 13, 2007; 6 pages.

* cited by examiner

*Primary Examiner* — Shanon A Foley
*Assistant Examiner* — Sarah Al-Awadi
(74) *Attorney, Agent, or Firm* — Grossman, Tucker, Perreault & Pfleger, PLLC

(57) ABSTRACT

A dermatological composition which may be used for the topical treatment of the skin, hair, or nails of mammals, comprising tamanu oil, an unsaturated fatty acid, and arnica oil, optionally including Vitamins E and A. The dermatological composition may be combined with other components to form a shampoo, conditioner, lotion, cream, spray, salve, or other cosmetic product in liquid, paste, or powder form.

6 Claims, No Drawings

TAMANU OIL PRODUCTS

FIELD OF THE INVENTION

The present invention relates to dermatologic compositions made with tamanu oil and other components which may be used for the topical treatment of the skin, hair, or nails of mammals. The compositions may find particular utility in hypoallergenic, grooming, anti-itch, and shed and dander control shampoos, conditioners, lotions, creams, sprays, or salves. General purpose dermatologic applications are also contemplated herein.

BACKGROUND OF THE INVENTION

Tamanu oil, botanical names *Calophyllum tacamahaca* or *Calophyllum inophyllum*, may be extracted by a cold pressed method from the tamanu tree whole nut. A typical sample of tamanu oil is dark green in color and contains both free fatty acids and fatty acids such as oleic, palmitic, linoleic, linolenic, and stearic acids. Tamanu oil is reported for use with respect to certain antimicrobial and antibiotic properties. For example, U.S. Pat. No. 5,906,825 teaches that *Calophyllum inophylloide* may be incorporated into a polymeric material to inhibit the growth of microorganisms in close proximity to the polymeric material. Tamanu oil is also reported for use with respect to certain anti-inflammatory and antioxidant properties. Tamanu oil is further reported for use with respect to certain therapeutic properties such as skin repair, scar healing, and tissue regeneration. Controlling tamanu oil concentrations and delivery protocols remains an ongoing area of research and development.

SUMMARY OF THE INVENTION

In one exemplary embodiment, the present invention is directed towards a dermatological composition that incorporates a controlled concentration of tamanu oil and other components. The composition may be combined with various other components to form cosmetic products including but not limited to shampoos, conditioners, lotions, creams, sprays, or salves. The composition may be applied topically to the skin, hair, or nails of mammals, preferably but not limited to dogs and other domestic animals.

DETAILED DESCRIPTION OF THE INVENTION

The present invention is a dermological composition that incorporates a controlled concentration of tamanu oil, an unsaturated fatty acid and arnica oil. The composition may also include one or a plurality of vitamins. The composition may be provided in a concentrated form and may therefore be blended with other components to provide shampoos, conditioners, lotions, creams, sprays, or salves. The composition blended with other components may further provide other products for topical application for dermis (skin), hair, or nails in liquid, paste, or powder form. Cosmetic products containing a controlled concentration of tamanu oil and the indicated components may find utility as, e.g., an all-purpose shampoo or conditioner, a relatively gentle shampoo that may be hypoallergenic, or a shampoo for the treatment of itchy skin, shedding, or dander, all of which may be suitable for use on small mammals such as dogs or puppies. A tamanu oil formulation may additionally find utility in sprays for general grooming.

The concentrated form of the dermatological composition may include but is not limited to the following components in the following concentrations, where expressed ranges include all values and increments therebetween:

20-80% by weight of Tamanu Oil;
0.05-30% by weight of an unsaturated fatty acid; and
0.05-20% by weight of Arnica Oil.

The unsaturated fatty acid may be a monounsaturated fat, a polyunsaturated fat, or a mixture thereof. Possible monounsaturated fats include but are not limited to tetradecenoic acid (common name myristoleic acid), pentadecenoic acid, hexadecenoic acid (common name palmitoleic acid), heptadecenoic acid, octadecenoic acid (common name oleic acid), eicosenoic acid (common name gadoleic acid), docosenoic acid (common name erucic acid), cis-tetracosenoic acid (common name nervonic acid), or mixtures thereof. Possible polyunsaturated fats include but are not limited to hexadecadienoic acid, octadecadienoic acid (common name linoleic acid), octadecatrienoic acid (common name linolenic acid), alpha-linolenic acid, gamma-linolenic acid, octadecatetraenoic acid (common name parinaric acid), eicosadienoic acid, eicosatrienoic acid, eicosatetraenoic acid (common name arachidonic acid), eicosapentaenoic acid (common name EPA or timnodonic acid), docosadienoic acid (common name brassic acid), docosapentaenoic acid (common name DPA or clupanodonic acid), docosahexaenoic acid (common name DHA), or mixtures thereof. In one embodiment, the unsaturated fatty acid may be a polyunsaturated fat such as linoleic acid.

The concentrated blend may further include one or a plurality of vitamins. In one embodiment, the concentrated blend may include 0.05-5% by weight of Vitamin E Acetate and/or 0.05-5% by weight of Vitamin A Palmitate, where expressed ranges include all values and increments therebetween.

The concentrated blend may be blended with other components in an aqueous-based solution to provide cosmetic products such as shampoos, conditioners, lotions, creams, sprays, or salves, of which the concentrated blend may make up a maximum of 5.0% by weight, including all values and increments. The products may contain 25-95% by weight of water, again including all values and increments therebetween. The following non-limiting examples of the concentrated blend as a component of various products for small mammals such as dogs and other domestic animals additionally illustrate the present invention.

Example 1

The concentrated form of the dermatological composition may be blended in an aqueous-based solution with one or more of the following components of an all-purpose shampoo. It may be appreciated that component concentrations may be varied from those indicated. The all-purpose shampoo may contain a maximum of 5% by weight of the concentrated blend, 25-95% by weight of water, 20-45% by weight of Sodium Laureth Sulfate, and a maximum of 45% by weight of Cocamidopropyl Betaine, where expressed ranges include all values and increments therebetween. Further, the all-purpose shampoo may contain a maximum of 10% of any other component indicated in Example 1, again including all values and increments, the components including:

Tetrasodium EDTA
Phenoxyethanol (and) Caprylyl Glycol (and) Ethylhexylglycerin (and) Hexylene Glycol
Glycerin
PEG-7 Glyceryl Cocoate
Cocamide MEA
Trimethylsiloxyamodimethicone (and) C11-15 Pareth-7 (and) C12-16 Pareth-9 (and) Glycerin (and) Trideceth-12

Lauryl Glucoside
Polysorbate 80
Awapuhi & Coconut Fragrance
Sodium Bicarbonate
Butylene Glycol (and) Water (and) Aloe Barbadensis Leaf Extract
Butylene Glycol (and) Water (and) Chamomilla Recutita (Matricaria) Flower Extract
Hydrolyzed Wheat Protein
Hydrolyzed Silk
DMDM Hydantoin
Citric Acid Example 2

The concentrated form of the dermatological composition may be blended in an aqueous-based solution with one or more of the following components of an all-purpose conditioner. It may be appreciated that component concentrations may be varied from those indicated. The all-purpose conditioner may contain a maximum of 5% by weight of the concentrated blend and 25-95% by weight of water, where expressed ranges include all values and increments therebetween. Further, the all-purpose conditioner may contain a maximum of 10% of any other component indicated in Example 2, again including all values and increments, the components including:
Disodium EDTA
Phenoxyethanol (and) Caprylyl Glycol (and) Ethylhexylglycerin (and) Hexylene Glycol
Glycerin
Behentrimonium Chloride
C15-19 Alkane
Triticum Vulgare (Wheat) Germ Oil
Tocopheryl Acetate
Cetyl Alcohol
Butyrospermum Parkii (Shea Butter)
Cetearyl Alcohol (and) Polysorbate 60
Green Tea Cucumber Fragrance
Farnesol
Hydrolyzed Wheat Protein
Hydrolyzed Silk
Butylene Glycol (and) Water (and) Aloe Barbadensis Leaf Extract
Butylene Glycol (and) Water (and) Chamomilla Recutita (Matricaria) Flower Extract
DMDM Hydantoin Example 3

The concentrated form of the dermatological composition may be blended in an aqueous-based solution with one or more of the following components of a shed and dander control shampoo. It may be appreciated that component concentrations may be varied from those indicated. The shed and dander control shampoo may contain a maximum of 5% by weight of the concentrated blend, 25-95% by weight of water, 20-45% by weight of Sodium Laureth Sulfate, and a maximum of 45% by weight of Cocamidopropyl Betaine, where expressed ranges include all values and increments therebetween. Further, the shed and dander control shampoo may contain a maximum of 10% of any other component indicated in Example 3, again including all values and increments, the components including:
Tetrasodium EDTA
Phenoxyethanol (and) Caprylyl Glycol (and) Ethylhexylglycerin (and) Hexylene Glycol
Glycerin
PEG-120 Methyl Glucose Dioleate
Glycol Distearate
Butyl Avocadate
Cocamide MEA
Cetearyl Alcohol (and) Polysorbate 60
Sodium PEG-7 Olive Oil Carboxylate
Green Tea Cucumber Fragrance
Farnesol
Butylene Glycol (and) Water (and) Aloe Barbadensis Leaf Extract
Butylene Glycol (and) Water (and) Chamomilla Recutita (Matricaria) Flower Extract
Glycerin (and) Triticum Vulgare (Wheat) Gluten (and) Water
DMDM Hydantoin Example 4

The concentrated form of the dermatological composition may be blended in an aqueous-based solution with one or more of the following components of an anti-itch spray. It may be appreciated that component concentrations may be varied from those indicated. The anti-itch spray may contain a maximum of 5% by weight of the concentrated blend and 25-95% by weight of water, where expressed ranges include all values and increments therebetween. Further, the anti-itch spray may contain a maximum of 10% of any other component indicated in Example 4, again including all values and increments, the components including:
Tetrasodium EDTA
Phenoxyethanol (and) Caprylyl Glycol (and) Ethylhexylglycerin (and) Hexylene Glycol
Honey
Butylene Glycol
Jojoba Wax PEG-120 Esters
Trideceth-12
PEG-7 Glyceryl Cocoate
Water (and) Butylene Glycol (and) Avena Sativa (Oat) Kernel Extract
Butylene Glycol (and) Pentylene Glycol (and) Dihydroavenanthramide D
Epilobium Angustifolium Extract
Butylene Glycol (and) Water (and) Aloe Barbadensis Leaf Extract
Butylene Glycol (and) Water (and) Chamomilla Recutita (Matricaria) Flower Extract
Butylene Glycol (and) Water (and) Althaea Officinalis (Marshmallow) Root Extract
DMDM Hydantoin Example 5

The concentrated form of the dermatological composition may be blended in an aqueous-based solution with one or more of the following components of a grooming spray. It may be appreciated that component concentrations may be varied from those indicated. The grooming spray may contain a maximum of 5% by weight of the concentrated blend and 25-95% by weight of water, where expressed ranges include all values and increments therebetween. Further, the grooming spray may contain a maximum of 10% of any other component indicated in Example 5, again including all values and increments, the components including:
Disodium EDTA
Phenoxyethanol (and) Caprylyl Glycol (and) Ethylhexylglycerin (and) Hexylene Glycol PEG-4
Coco Glucoside (and) Glyceryl Oleate
Trideceth-12
PEG-7 Glyceryl Cocoate
Triticum Vulgare (Wheat) Germ Oil
Tocopheryl Acetate
Green Tea Cucumber Fragrance
Sodium Bicarbonate
Hydrolyzed Silk
Hydrolyzed Wheat Protein
Butylene Glycol (and) Water (and) Aloe Barbadensis Leaf Extract
Butylene Glycol (and) Water (and) Chamomilla Recutita (Matricaria) Flower Extract
Butylene Glycol (and) Water (and) Rosmarinus Officinalis (Rosemary) Leaf Extract
Polyquaternium-10
DMDM Hydantoin Example 6

The concentrated form of the dermatological composition may be blended in an aqueous-based solution with one or more of the following components of a shampoo for the treatment of itchy skin. It may be appreciated that component concentrations may be varied from those indicated. The anti-itch shampoo may contain a maximum of 5% by weight of the concentrated blend, 25-95% by weight of water, a maximum of 20% by weight of Magnesium Aluminum Silicate, a maximum of 45% by weight of Cocamidopropyl Betaine, and a maximum of 20% by weight of Sodium Trideceth Sulfate, where expressed ranges include all values and increments therebetween. Further, the anti-itch shampoo may contain a maximum of 10% of any other component indicated in Example 6, again including all values and increments, the components including:
Tetrasodium EDTA
Phenoxyethanol (and) Caprylyl Glycol (and) Ethylhexylglycerin (and) Hexylene Glycol
Honey
Glycol Distearate
Cocamide MEA
PEG-150 Distearate
Poloxamer 184
Polysorbate 80
Farnesol
Green Tea Cucumber Fragrance
Butylene Glycol (and) Water (and) Aloe Barbadensis Leaf Extract
Epilobium Angustifolium Extract
Water (and) Butylene Glycol (and) Avena Sativa (Oat) Kernel Extract
DMDM Hydantoin Example 7

The concentrated form of the dermatological composition may be blended in an aqueous-based solution with one or more of the following components of a relatively gentle shampoo that may be hypoallergenic. It may be appreciated that component concentrations may be varied from those indicated. The shampoo may contain a maximum of 5% by weight of the concentrated blend, 25-95% by weight of water, a maximum of 45% by weight of Cocamidopropyl Betaine, and a maximum of 20% by weight of Sodium Trideceth Sulfate, where expressed ranges include all values and increments therebetween. Further, the shampoo may contain a maximum of 10% of any other component indicated in Example 7, again including all values and increments, the components including:
Tetrasodium EDTA
Phenoxyethanol (and) Caprylyl Glycol (and) Ethylhexylglycerin (and) Hexylene Glycol
PEG-150 Distearate
PEG-7 Glyceryl Cocoate
Sodium Laurylglucosides Hydroxypropylsulfonate
Polysorbate 80
Green Tea Cucumber Fragrance
Butylene Glycol (and) Water (and) Aloe Barbadensis Leaf Extract
Butylene Glycol (and) Water (and) Chamomilla Recutita (Matricaria) Flower Extract
Butylene Glycol (and) Water (and) Avena Sativa (Oat) Kernel Extract
DMDM Hydantoin Example 8

It may be appreciated that the components and concentrations indicated in Examples 1 through 7 may be varied and interchanged among cosmetic formulations. Further, component concentrations may vary as additional components are blended into a cosmetic formulation. Possible additional components include but are not limited to Aloe Barbadensis Leaf Extract; Chamomilla Recutita (Matricaria) Flower Extract; Triticum Vulgare (Wheat) Germ Oil; Triticum Vulgare (Wheat) Gluten; Avena Sativa (Oat) Kernel Extract; Althaea Officinalis (Marshmallow) Root Extract; Glycyrrhiza Glabra (Licorice) Extract; Epilobium Angustifolium Extract; Squalane Extract; a cationic polymeric salt; a glycine; a soluble fiber; an anionic surfactant; a zinc salt; hydrolyzed silk; farnesol; and/or honey.

The cationic polymeric salt may be but is not limited to a water soluble cellulose derivative, such as polyquaternium-10. The glycine may be but is not limited to undecylenoyl glycine (sold under the trade name Lipacide® UG), capryloyl glycine (sold under the trade name Lipacide® C8G), or a mixture thereof. The soluble fiber may be but is not limited to one or a plurality of beta-glucans, such as those found in oats, barley, yeast, bacteria, algae, mushrooms, and other cereal grains. The anionic surfactant may be but is not limited to an olive-based surfactant, such as Sodium PEG-7 Olive Oil Carboxylate (sold under the trade name Olivem® 400). The zinc salt may be but is not limited to a zinc salt of L-Pyrrolidone Carboxylic Acid (sold under the trade name Zincidone®).

The foregoing description is provided to illustrate and explain the present invention. Furthermore, it should again be appreciated that the components and features within all of the working examples are interchangeable, and are not limited to the specific examples and/or specific products within any given example. In addition, the description hereinabove should not be considered to limit the scope of the invention set forth in the claims appended here to.

What is claimed is:

1. A dermatologic composition for the topical treatment of the skin, hair, or nails of mammals, comprising a maximum of 5.0% by weight of a mixture, wherein said mixture consists of:
20-80% by weight of Tamanu Oil;
0.05-30% by weight of an unsaturated fatty acid; and
0.05-20% by weight of Arnica Oil.

2. The composition of claim 1 wherein the unsaturated fatty acid is selected from the group consisting of tetradecenoic acid, pentadecenoic acid, hexadecenoic acid, heptadecenoic acid, octadecenoic acid, eicosenoic acid, docosenoic acid, cis-tetracosenoic acid, hexadecadienoic acid, octadecadienoic acid, octadecatrienoic acid, alpha-linolenic acid, gamma-linolenic acid, octadecatetraenoic acid, eicosadienoic acid, eicosatrienoic acid, eicosatetraenoic acid, eicosapentaenoic acid, docosadienoic acid, docosapentaenoic acid, docosahexaenoic acid, and mixtures thereof.

3. The composition of claim 1 wherein said mixture is combined with 25-95% by weight of water.

4. The composition of claim 1 in the form of a shampoo, conditioner, lotion, cream, spray, or salve.

5. The composition of claim 1 as a topical application for dermis, hair, or nails in liquid, paste, or powder form.

6. A dermatologic composition for the topical treatment of the skin, hair, or nails of mammals, comprising a maximum of 5.0% by weight of a mixture, wherein said mixture consists of:

20-80% by weight of Tamanu Oil;
0.05-30% by weight of an unsaturated fatty acid; and
0.05-20% by weight of Arnica Oil
wherein said mixture is combined with one or more of the following additional components in an aqueous-based solution: *Aloe Barbadensis* Leaf Extract; *Chamomilla Recutita* (*Matricaria*) Flower Extract; *Triticum Vulgare* (Wheat) Germ Oil; *Triticum Vulgare* (Wheat) Gluten; *Avena Sativa* (Oat) Kernel Extract; *Althaea Officinalis* (Marshmallow) Root Extract; *Glycyrrhiza Glabra* (Licorice) Extract; *Epilobium Angustifolium* Extract; Squalane Extract; a cationic polymeric salt; a glycine; a soluble fiber; an anionic surfactant; a zinc salt; hydrolyzed silk; farnesol; honey.

* * * * *